United States Patent [19]
Glennie et al.

[11] Patent Number: 5,800,364
[45] Date of Patent: Sep. 1, 1998

[54] FOOT ORTHOSES

[75] Inventors: Kenneth Donald Glennie, Deeside; William Alan Turner, Bucks, both of United Kingdom

[73] Assignee: Orthotics Limited, United Kingdom

[21] Appl. No.: 513,894

[22] PCT Filed: Mar. 1, 1994

[86] PCT No.: PCT/GB94/00396
§ 371 Date: Feb. 20, 1996
§ 102(e) Date: Feb. 20, 1996

[87] PCT Pub. No.: WO94/20020
PCT Pub. Date: Sep. 15, 1994

[30] Foreign Application Priority Data

Mar. 1, 1993 [GB] United Kingdom ............ 9304058

[51] Int. Cl.$^6$ ............................................. A61B 5/103
[52] U.S. Cl. ........................................ 600/592; 600/595
[58] Field of Search ............................. 128/799, 782, 128/774

[56] References Cited

U.S. PATENT DOCUMENTS 4,267,728  5/1981  Manley et al. .
4,686,993  8/1987  Grumbine .
4,813,436  3/1989  Au .

FOREIGN PATENT DOCUMENTS 0074231   3/1983   European Pat. Off. .
WO 91/17708  11/1991  WIPO .

OTHER PUBLICATIONS

Begg et al. (1991) Clin. Biomechanics 6:168–72.

*Primary Examiner*—Max Hindenburg
*Assistant Examiner*—Pamela L. Wingard
*Attorney, Agent, or Firm*—Kluber & Jackson

[57] ABSTRACT

The invention provides an apparatus and method for recording characteristics of a person's foot and for interpreting the results to design a function foot orthosis. As the person undergoes a movement routine, video cameras (24, 26, 28, 30) view the person's foot in real time from below, from the front, from the right side and from the rear to produce simultaneous images which together give a three-dimensional record of the person's foot. During analysis, selected video images from the recordings are calibrated and analyzed geometrically to ascertain the characteristics of the person's foot. A functional orthotic is designed and manufactured by computer-aided apparatus.

19 Claims, 7 Drawing Sheets

FOOT ORTHOSES

This invention relates to apparatus and methods for use in the prescription, design and production of biomechanical functional foot orthoses.

Such orthoses can be used to compensate for, and to control, abnormal movement of, and within, a person's foot or feet. The orthosis is a customised insert which fits into the person's shoe or other footwear and is effective in exercising the desired control to the foot.

However, difficulties exist in the current techniques for determining the design of an appropriate orthosis to suit an individual foot. If the shape of the orthosis is inappropriate, the orthosis may not achieve the desired control over the person's foot, and it may even cause distress to the person using the orthoses.

Before an orthosis can be prescribed for a foot, it is necessary to measure the characteristics of the foot. This is usually done by a prescribing practitioner identifying predetermined reference points on the foot and marking these on the skin with a pen. Distances between certain points are then measured, and angles between lines joining the points are measured with a protractor or other instrument. A major problem with this technique is that it can be difficult to determine the exact positions of the reference points to mark on the foot. Further inaccuracies are caused by skin movement over the underlying bones of the foot, and difficulties in keeping the foot absolutely still in the appropriate position to take the measurements.

In view of the known difficulties in pin-pointing the reference points on the foot, a system of approximate points has been devised in which the points are, in general, easier to determine for each individual foot. It is then left to the fabrication laboratory at which the orthoses are manufactured to make estimate corrections to the measurements taken by the prescribing practitioner.

Although this simplifies the procedure for the practitioner, it represents a further source of inaccuracy.

When prescribing a design for an orthotic device, the prescription instruction usually comes from a standard neutral position cast (S.T.J.N.) with the forefoot maximally pronated on the rearfoot. The cast is usually plaster of paris bandage, and the final casting position is maintained by the prescribing practitioner physically holding the person's foot in a predetermined position. The neutral position has been defined as a standard reference position from which the deviation of the person's foot from "normal" can be quantified.

As an alternative to casting, another known technique involves the practitioner holding the person's foot in a predetermined stationary position while its profile is determined by a scanning laser beam.

Both of the above techniques suffer disadvantages in that they only study the foot in one stationary position. Kinetic measurements, for example, the range of available movement, cannot be made accurately, and consequently these have to be estimated by the prescribing practitioner. It can also be difficult, especially with children or with the elderly, to remain absolutely still for long enough to obtain an accurate cast or scan.

In the case of casts, it has been found that up to 75–80% of prescription casts are incorrect, and have to be corrected at the fabrication laboratories where the functional orthoses are made. Such a high rate of error is very unsatisfactory and can lead to further errors in an attempt to correct the original mistakes.

A further known technique for studying a person's foot is to place small adhesive pressure transducers on the foot, so as to monitor directly 3-dimensional forces with time, as the patient moves about. However, as well as being incapable of detecting rotational forces, this system is subject to movement of the skin on which the sensors are placed. The system also relies on significant assumptions being made regarding forces within the foot and regarding the position and orientation of the foot.

Established processes for the manufacture of the orthoses have often included many process stages, each requiring supervision by control personnel. With such processes it can be difficult to achieve the appropriate material thickness for resilience or rigidity as desired, and to produce an orthotic device which fits the person's foot and footwear comfortably.

More recently it has been proposed to improve the manufacturing process by using computer-aided modelling and milling. However, current foot diagnosis and measurement techniques still require refinement to match such accuracy.

The present invention has been devised with the above problems in mind.

In a first aspect, the invention provides a method of measuring orthotic characteristics of a person's foot, comprising:

providing a plurality of video cameras for viewing the foot from a plurality of different look directions;

recording the shape and appearance of the foot substantially in real time by using the video cameras concurrently to provide video images containing information in three dimensions; and analysing the video images to obtain the desired measurements.

By using video cameras, the shape and appearance of the foot can be recorded quickly and easily without requiring the person to hold his or her foot still for long periods of time. The accuracy of the video images will depend on the resolution of the cameras, and on their focusing. High resolution cameras with auto-focusing are available which are not too expensive.

Preferably, the video cameras are positioned to view the foot from positions which are at 90° to the cardinal body planes. The cardinal body planes correspond to the major axes of the human body, called the Transverse, Frontal and Coronal (or Sagital) directions.

It will be appreciated that any number of cameras may be used as desired, in order to produce images from desired look directions. The cameras are preferably adjustable to enable the camera position and look direction to be varied as desired.

Preferably the images are analysed and calibrated using a computer based video image processing system. Preferably, the video system allows one or more of the following functions to be performed: (i) video images can be stored in a digital framestore; (ii) the images can be viewed in slow motion, frame by frame; (iii) selected portions of the images can be magnified or enhanced for contrast; and (iv) the geometry of features in an image can be measured, ie. distances and angles.

Such a system can provide repeatable, accurate measurements without relying on assumptions or approximations as in the prior art. The data provided by the measurements and the foot images can easily be put into a form suitable for three-dimensional modelling for the design of the orthosis.

Preferably, the method includes exercising the foot through a plurality of predetermined positions and motions, while in the view of the cameras. Thus the method records not only an instantaneous stationary position of the person's foot, but also its movement.

Preferably, the exercise includes open and closed kinetic chain positions. Preferably, the exercise also includes subjecting the person's foot to controlled stress.

Thus, the method of the invention enables a record to be made of the available movement of the foot, and of the foot's appearance or condition when in various positions.

Preferably, a first of the video cameras is provided to view the underside of the person's foot. The first video camera may comprise a stereo imaging camera to provide a contour image of the sole.

Preferably, a second of the video cameras is provided to view a side, or the front or the rear of the foot. Several such cameras may be provided, one each to view the front, rear and side of the foot.

One or more (or all) of the cameras may be movable, so that they can be adjusted relative to the person's foot, ie. the camera's position and look direction may be varied.

Preferably, the output signals of the cameras are combined to form a multiplexed signal containing multiple images. The combined signal may, for example, correspond to four images arranged in four respective quadrants of a display. The use of a multiplexed signal avoids possible problems in time synchronisation which might occur if the images were to be processed and recorded as separate signals.

Preferably, the step of recording comprises recording the output video signals, or the combined signal, on to one or more video signal recording mediums. In the preferred method, a combined output signal is recorded on to a single recording medium, such as video tape.

Preferably, the method includes indexing the signals recorded on the recording medium or mediums according to a particular foot exercise which the person is performing.

For example, the indexing may comprise inserting a code in, or applying a colour tint or a colour wash to, the signals being recorded.

The method may also comprise presenting a prerecorded demonstration audio and/or video recording to instruct the person through a foot movement routine. In such a case, the indexing is preferably controlled by control signals in the prerecorded demonstration recording.

One of the cameras may comprise a thermal camera to detect "hot spots" on the patient's body. As a further alternative a dedicated thermal camera could be provided in addition to the above cameras.

In a second closely related aspect, the invention provides a method for making a record of a person's foot for a functional orthosis, comprising providing a first video camera to view the foot from the underside;

providing a second video camera to view the foot from the rear;

providing a third video camera to view the foot from a side;

providing a fourth video camera to view the foot from the front; and recording the shape and appearance of the foot substantially in real time by using the video cameras concurrently to provide video images containing information in three dimensions.

Preferably one or more (or all) of the cameras are movable so that they can be adjusted relative to the person's foot. Preferably, the cameras are positioned or adjusted to view the foot from positions which are at 90° to the cardinal body planes.

Preferably, the method includes exercising the foot through a plurality of predetermined positions, motions and stresses, as explained hereinbefore.

Preferably, the method further comprises combining the output signals from the cameras to form a multiplexed signal containing multiple images, as explained hereinbefore.

Preferably, the method further comprises indexing the signals, for example by using a colour tint, as explained hereinbefore.

Preferably, the method further comprises presenting a prerecorded demonstration film to instruct the person through a foot movement routine. In such a case, the indexing is preferably controlled from the demonstration film.

The method may also comprise providing controlled lighting to illuminate the person's foot during recording. The lighting may be controlled to be varied during the recording process to provide optimum lighting for the person's particular foot position or foot exercise. For example, in certain cases it might be found that light shining into a camera from the opposite side of a person's foot can "blind" the camera, or reduce its effective contrast. An example of a possible problem might be illuminating the person's foot from above when it is desired to obtain detail of the underside of the person's foot. In such a case, it would be desirable to illuminate the person's foot from below rather than from above. Therefore, the method may comprise providing light from one direction during certain intervals of the recording process, and providing light from one or more other directions during one or more other intervals. Preferably, the method further comprises controlling the lighting in response to control signals in the prerecorded demonstration recording.

Preferably, the method further comprises providing visual markers on the person's foot. For example, manual stick-on markers or a marker sheet could be used. Alternatively, the method may comprise projecting light markers or light-shadow markers on to the foot. For example, a grid arrangement of dots could be projected to create a grid image of dots on the person's foot. Such an arrangement could provide additional reference points to enhance the visibility during the analysis of the video recordings, also to enhance the 3-dimensional shape of the foot, and to assist in pinpointing the precise position of selected points on the foot. Preferably, the method further comprises controlling the projection of visual markers in response to signals in the prerecorded demonstration recording.

The light sources for the lighting and for the light projection may be chosen as desired to produce the appropriate lighting effect. For example, laser lighting or projection may be used.

Preferably, the method comprises recording the video images on a video recording medium, either separately or as multiplexed signal. The latter signal avoids the possibility of time synchronisation problems during playback.

In a third closely related aspect, the invention provides an apparatus for making a record of a person's foot for a functional orthosis, comprising:

a platform on which a person may stand or may place the foot to be recorded, at least a portion of the platform being transparent;

a first video camera at a first position to view the underside of the foot through the transparent portion of the platform;

a second video camera at a second position for viewing the foot from the rear;

a third video camera at a third position for viewing the foot from a side;

a fourth video camera at a fourth position for viewing the foot from the front; and means for operating the cameras concurrently for recording the shape and appearances of the foot substantially in real time to provide video images containing information in three dimensions.

Preferably, at least the second, third and fourth video cameras are movable relative to the platform so that they can be positioned relative to the person's foot at optimum orientations to view the foot from the rear, side and front, respectively. Preferably, the cameras view the foot from positions which are at 90° to the cardinal body planes.

This enables account to be taken of the different feet positions which people adopt. For example, one person may stand naturally with his or her feet splayed outwardly, while another person may stand with his or her feet parallel. In the preferred embodiment, the second, third and fourth cameras are in fixed angular positions relative to each other, spaced apart by about 90°. This ensures that when, for example, the second camera is positioned appropriately to view the rear of the foot, the third and fourth cameras will be lined-up automatically to view the side and front of the foot, respectively. The cameras are capable of limited arcuate movement together around the intended position of the person's foot on the platform. Preferably, all the cameras are movable. Preferably each camera can be adjusted to view in any selected direction.

Preferably, at least one of the second, third and fourth video cameras is capable of being inclined relative to the platform to view along an elevated look direction, for example, up to the person's knee. This enables the person's lower body movement to be observed during the foot exercises, which can give information about abnormalities in gait and stance.

Preferably, the platform is marked with a graticule grid. This can assist in calibrating the video images during analysis.

Preferably, the apparatus comprises a multiplexer for combining the signals from the video cameras to form a multiplexed signal. For example, the images in the four video signals may be reduced in size, and multiplexed to appear in respective quadrants of a combined "frame".

Preferably, the apparatus further comprises indexing means for applying or inserting an index code or signal to one or more of the four video signals. The index code or signal indicates which particular form of foot exercise was being performed at the time the images were recorded by the video cameras. In the preferred embodiment, the indexing means applies a colour tint to the video images, the colour being variable.

Preferably, the apparatus further comprises an audio/video monitor and a playback apparatus for presenting a pre-recorded demonstration or instruction film to guide the person through a pre-planned foot movement routine. Preferably, the apparatus comprises means responsive to control signals in the pre-recorded film to control the index signal applied by the indexing means.

Preferably, the apparatus comprises means for recording the video image signals, or the multiplexed signal, on a video recording medium. In the preferred embodiment, the multiplexed signal is recorded on to a single recording medium, such as video tape.

The first video camera may comprise a stereo imaging camera to provide a three dimensional contour image of the sole of the person's foot. The output signal from the camera would include a colour component indicative of the distance from the camera. The indexing means would then be controlled not to adjust the colour component from the first camera.

More than four video cameras may be provided, as desired. For example, if detail of the person's upper body movement is required, additional cameras may be used to record this.

A treadmill or a walkway may also be used in association with the recording apparatus, in order to observe a person's foot movement while walking or running. To avoid vibrations being transmitted to the video cameras which could introduce image jitter, the cameras might be isolated from the treadmill or walkway, for example, using vibration absorbing supports.

Preferably, the apparatus further comprises controllable lighting to illuminate the person's foot. Preferably, the lighting comprises means for providing light to illuminate the foot from a plurality of selectable directions. For example, this may comprise a first controllable light source for illuminating the foot from above, and a second controllable light source for illuminating the person's foot from below. Preferably, the apparatus further comprises means for controlling the lighting in response to control signals in the pre-recorded film to provide fixed or varying lighting to suit each particular foot exercise being performed. A manual control could also be provided.

To improve the 3-dimensional accuracy of the calibration and analysis, visual markers may be arranged on the person's foot. For example, manual stick-on markers or a marker sheet could be used. Alternatively, light-shadow markers could be projected onto the foot by means of a light projector. The markers would provide additional reference points to enhance visibility during the analysis of the video recordings, also to enhance the 3-dimensional shape of the foot, and to assist in pin-pointing the precise position of selected points on the foot. Preferably, the apparatus comprises a light, or light-shadow, image projector which is controlled in response to control signals in the pre-recorded film. A manual control could also be provided.

Preferably, the apparatus comprises means for identifying the regions of contact of a person's foot on the platform. In a preferred form, such means comprise means for illuminating the platform in such a manner that the areas of contact are highlighted when the foot is in view from below the platform. Preferably, the apparatus comprises means for introducing light into the transparent portion of the platform, such that the light will be refracted/reflected differently at the "foot contact" areas in order to produce a different visual effect at these contact areas. In the preferred embodiment, the platform is made of perspex, and light is introduced at one edge of the platform to illuminate the material within the platform. When a person stands on the platform, the areas of contact appear as significantly lighter regions, whereas regions where there is no genuine contact appear as normal brightness. The effect is believed to result from the contact or pressure of the person's foot when standing on the platform affecting the interior and surface refraction/reflection characteristics of the material, which in turn produces a light image pattern. Materials other than perspex (eg. acetate) may be used to form the platform while still achieving the same visual effect.

The above principles of the invention also permit new techniques for analysing details of a person's foot.

In a fourth aspect, the invention provides a method for determining characteristics of a person's foot, comprising:
providing a sequence of video images frame by frame of a person's foot;
selecting a frame for analysis;
defining predetermined points on the image depicted in the frame selected for analysis; and calculating mathematically one or more geometric characteristics of the person's foot based on the points defined in the image.

Thus, the values of predefined geometric characteristics or parameters which describe a person's foot can be calculated by measuring points on the video image of the person's foot. The method allows a particular frame to be selected which typifies the optimum shape or position of the foot for calculating a characteristic.

In the preferred embodiment, the step of calculating is performed automatically within a computer based video image processing system. The accuracy is determined by: (i) the resolution of the image frame; (ii) the resolution of the computer based system; and (iii) the calibration of the system for measuring distances between selected pixel points in the video image.

Preferably, to achieve accurate calibration, at least one of the video frames includes a linear calibration scale relating to the size of the foot depicted in the video images and the method includes obtaining a calibration from the calibration scale prior to calculating the one or more characteristics.

Preferably, each video frame or "instant" includes a plurality of images displayed concurrently and obtained from different look directions, and the method comprises selecting a frame for analysis based on a first of the plurality of images, and using a second of the plurality of images to calculate the one or more characteristics. By this method, it is possible to select only the appropriate frames, which satisfy several criteria to obtain accurate measurements.

In a fifth aspect, the invention provides apparatus for determining characteristics of a person's foot comprising:

means for providing a sequence of video images of the foot frame by frame;

means for selecting a frame for analysis;

means for defining predetermined points on the image depicted in the frame selected for analysis; and means for calculating mathematically one or more characteristics of the person's foot based on the points defined in the image.

Preferably, each frame includes a plurality of images, and the means for selecting comprises means for selecting one or more of the images for analysis from the frame.

Preferably, the apparatus comprises a digital pixel framestore in which the video frame or a selected video image is stored.

Preferably, the apparatus comprises a plurality of framestores in which video frames or selected video images can be stored for later use.

In a further aspect, the invention provides a method of diagnosing orthotic characteristics of a person's foot, comprising:

providing a sequence of video images frame by frame of the foot;

measuring geometric characteristics of the foot from one or more of the video frames; and comparing the measured geometric characteristics with a set of reference characteristics to determine deviation from normality.

Preferably the method further comprises operating an expert system to analyse the measured geometric characteristics, and to prescribe a functional orthosis.

An embodiment of the invention is now described by way of example, with reference to the accompanying drawings, in which:

FIG. 1 illustrates a process in accordance with this invention, for analysing a person's foot or feet, and for prescribing and manufacturing one or more suitable functional orthoses for that person.

The first stage 10 of the process is to make a record of each foot using a plurality of video cameras making simultaneous recordings from different look directions. As described below in more detail, the cameras run in real time, and are positioned to enable the movement, shape and appearance of foot to be viewed substantially three-dimensionally.

The second stage 12 of the process is to analyse the video recordings, and measure the geometric characteristics of each foot as seen in the video images. As described below in more detail, this involves selecting specific recorded images in which the foot is in one of a plurality of predetermined reference positions. The geometric characteristics can then be calculated by a computer-aided geometric analyser. Once the characteristics have been determined, an "expert system" is used to analyse the results, and to supply the appropriate design parameters for one or more compensatory functional orthoses.

The final stage 14 of the process is to manufacture each orthosis by using a computer controlled milling or manufacturing machine. The data for the machine can be supplied directly as a three-dimensional model calculated by the expert system, based on the shape of the person's foot as viewed in the video images. As an alternative, a manual manufacturing process could be used based on the data obtained from the recorded images.

Figure 1:
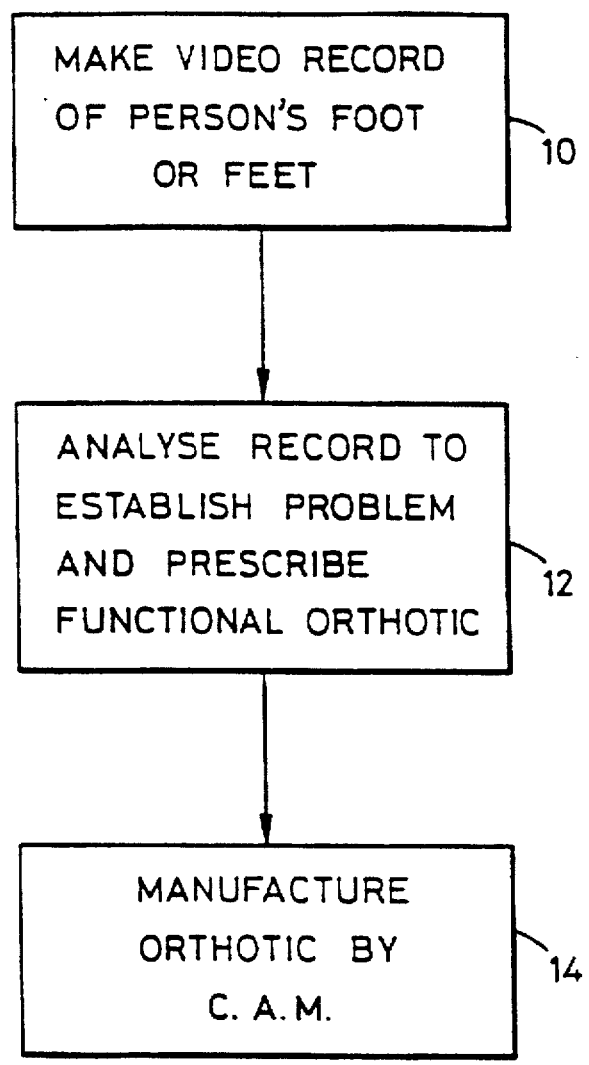
FIG. 1 is a block diagram of a process for prescribing/manufacturing functional orthoses.
Figure 2:
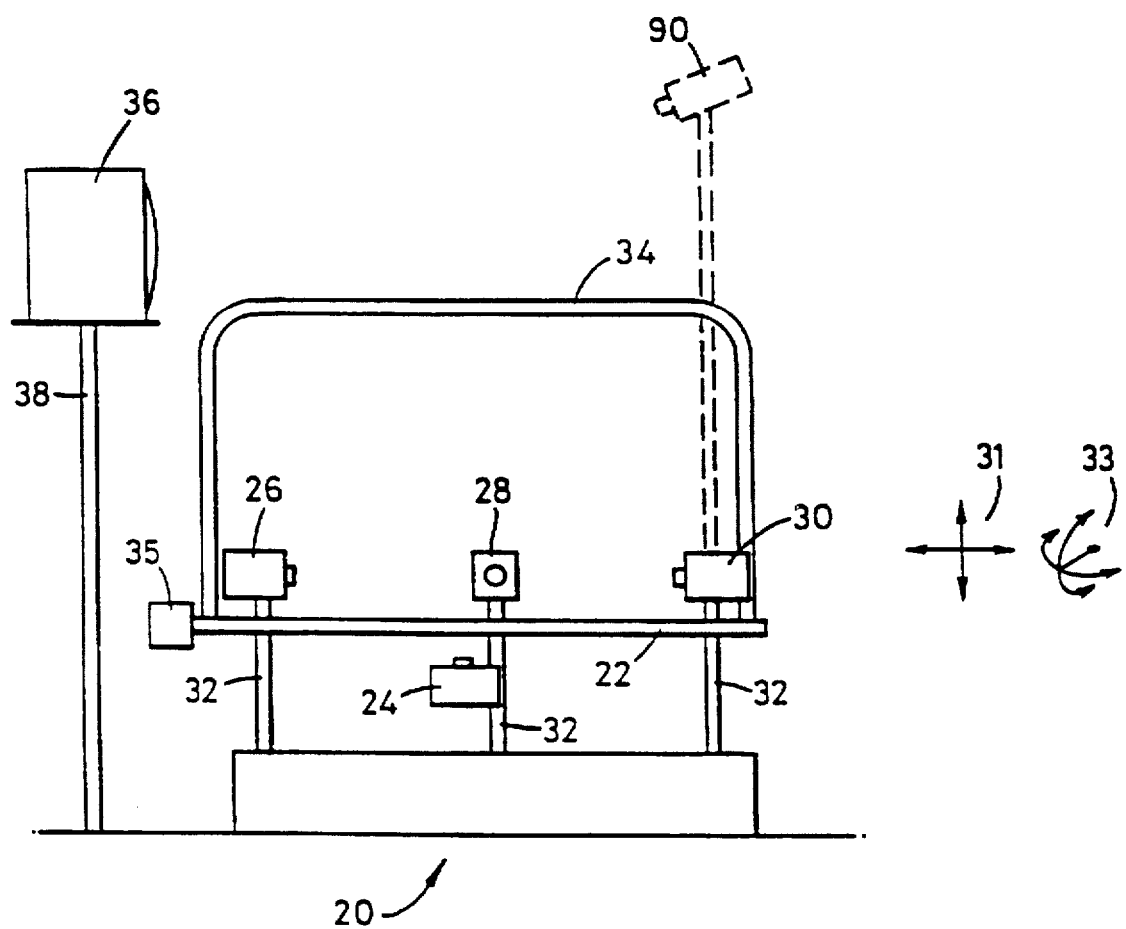
FIG. 2 is a schematic side view of an apparatus for making a record of a person's foot.
Figure 3:
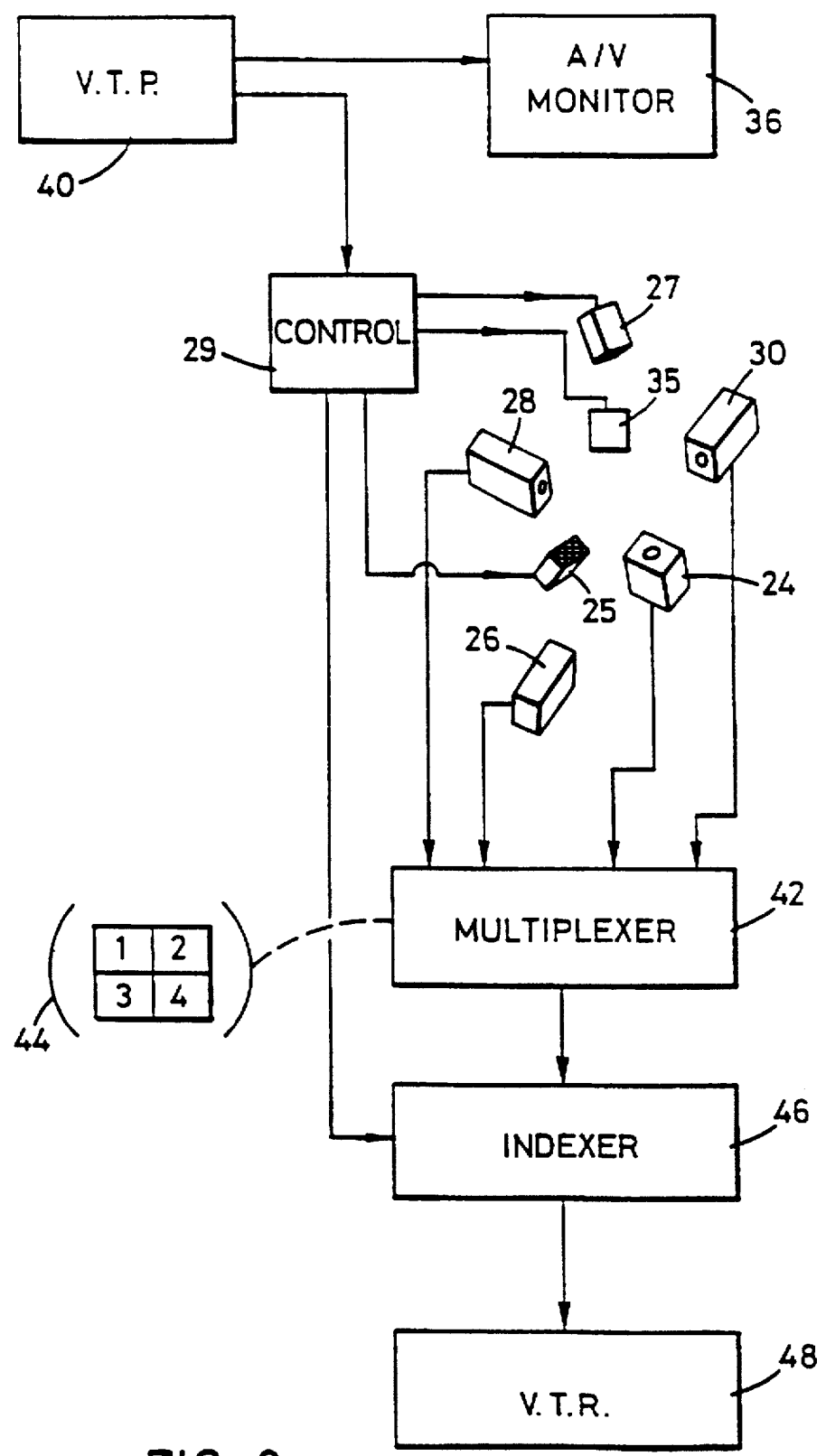
FIG. 3 is a block diagram of parts of the apparatus of FIG. 2.

FIGS. 2 and 3 illustrate an apparatus 20 for making the video recording of a person's foot. The apparatus 20 includes a transparent platform 22 on which the person stands barefooted. A first video camera 24 is mounted below the platform 22 in a first position to view the underside of the person's foot. A second video camera 26 is mounted at the level of the platform 22 in a second position to view the foot from the front. A third video camera 28 is mounted at the level of the platform 22 in a third position to view the foot from one side. A fourth video camera 30 is mounted at the level of the platform 22 in a fourth position to view the person's foot from the rear.

In this exemplary embodiment, the cameras 26, 28 and 30 above the platform 22 are movable in a plane substantially parallel to the platform 22. Each camera 26, 28 and 30 is mounted on a respective support 32 which extends through a respective arcuate slot (not shown) in the platform, such that the cameras are movable arcuately around the person's foot. The cameras 26, 28 and 30 are coupled for movement together to maintain their orientations relative to one another, and the range of movement is about 90°. In other embodiments, the cameras may be capable of other forms of movement relative to the platform, and relative to one another. In use, the cameras are positioned so that they view the foot from user selected positions, for example, at 90° to the cardinal body planes.

The camera 24 positioned below the platform 22 may comprise a stereo imaging camera which provides a 3-D contour of the surface being viewed, in this case the underside of the person's foot. The output from the stereo imaging camera may, for example, include a colour component indicative of the distance from the camera.

The camera 26 for viewing the person's foot from the front is preferably capable of viewing the person's leg up to and including the knee. This allows a record to be made of the person's stance, and gait when moving. The camera 26 is preferably inclinable so that its field of view can be elevated above the level of the platform. The other two cameras 28 and 30 above the platform may also be inclinable.

For maximum flexibility, the horizontal and vertical position of each camera, its rotational direction and its inclination, may be adjustable as depicted by the arrows 31 and 33.

A light projector 25 (not shown in FIG. 2) is provided to project light onto the underside of the person's foot. The projector may include a device to project markers in the form of light-shadows at predetermined positions. The projector is preferably adjustable to suit the sizes and shapes of different people's feet.

A second light projector 27 (not shown in FIG. 2) is provided to project light onto the person's foot from above. The light projectors 25 and 27 are controlled by a controller 29, described in more detail below.

The platform 22 is marked with a graticule grid (not shown) which is used for the purpose of calibrating the video images, and to permit calibrated stress measurements, as explained in more detail hereinafter.

In this exemplary embodiment the platform is made of transparent perspex, and comprises a slab or sheet approximately 2.5 cm (1 inch) in thickness. A light source 35 is arranged adjacent to one edge of the platform 22 in order to introduce light into the interior of the platform 22. This provides a visual effect to locate precisely the regions at which the person's foot is in contact with the platform 22. It is believed that the contact and/or pressure of the foot affects the internal and/or surface refraction/reflection characteristics of the material. The result is that the contact areas become significantly lighter (i.e. white) regions when viewed from below, and the surrounding non-contact region show as regions of normal brightness. It is thus possible to identify or record accurately which parts of the foot are flat against the platform, and which parts of the foot are not in contact. The light source 35 can be controlled automatically, as described hereinafter.

A guard rail 34 is provided around the platform 22 to prevent a person standing on the platform 22 from accidentally falling off when performing foot exercises.

An audio video monitor 36 is mounted on a movable arm or stand 38 in front of the platform 22. In use, a prerecorded demonstration or instruction film is presented on the monitor 36 from a video tape player 40. The film guides a person standing on the platform 22 through a series of pre-planned foot exercise routines. The video cameras 24, 26, 28 and 30 record the movement, shape and appearance of the person's foot substantially in real time as the person performs the routines. The routines are intended to put the person's foot through a range of stationary and kinetic positions, both stressed and unstressed, preferably using the whole range of available foot movement.

In this exemplary embodiment, the film also includes one or more control signals which are used to control operation of the recording apparatus during different intervals of the foot routine. An output from the tape player 40 is coupled to an input of the controller 29 to achieve this. As the demonstration film is run, the controller 29 receives instructions from the control signals encoded in the film to control the light projectors 25 and 27 to provide optimum lighting (and light-markers when appropriate) for the foot routine being performed, and also signals to control operation of the light source 35. The controller 29 also provides index control signals to control an indexer 46 described below.

The video cameras 24, 26, 28 and 30 have a high enough resolution to record the person's foot accurately. The frame scanning period for each camera should be as fast as possible so that blurring will not occur during foot movement. A scanning interval of about one thousandth of a second is appropriate. The frame rate for each camera should also be high, so that foot movement is recorded accurately. A frame rate of about 25 frames per second is acceptable. The cameras may be monochrome or colour, but it has been found that monochrome images may be easier to index and to analyse, as described hereinafter.

The output signals from the cameras 24, 26, 28 and 30 are fed to a signal multiplexer 42, which provides a single combined output signal. As illustrated at 44, the images from the cameras (labelled 1–4) are each reduced to a quarter of the frame size, and are arranged in respective quadrants of the frame. Therefore, each video frame of the combined output signal comprises the four camera images displayed concurrently. Depending on the number of video cameras being used, the multiplexer 42 may function to combine a greater (e.g. 8) or lesser (e.g. 2) number of signals into a single output signal.

The output from the signal multiplexer 42 is fed to an indexer 46 which inserts or applies an indexing signal or code to one or more of the four images in the frame. The index is used to identify which foot routine the person is performing at the time of recording. An output from the controller 29 is fed to a control input of the indexer 46 to control this. In the present exemplary embodiment, the indexer 46 applies a coloured tint to the video signal, the colour being variable and representing which foot routine is currently being performed. The use of a colour tint has the advantage that it does not interfere with the information content of the monochromatic signals, it can be easily recognised, and it does not require part of the useful video signal to be set aside for a dedicated index code. If a stereo imaging camera is used, the indexer would be arranged not to adjust the colour component of the image from the stereo imaging camera. As an alternative, the tint may be replaced by text or graphics (eg. a barcode) to indicate the current foot routine.

The output video signal from the indexer is ready to be analysed. In this embodiment, the signal is recorded on a high quality video recording medium, such as Hi-8, S-VHS or VHS tape. In other embodiments, the signal may be processed further, for example by a computer on the apparatus, or it may be transmitted directly to an external analysis station, for example, by a modem link.

It is also envisaged that the signal may be transmitted directly over a video cable, or transmitted as a telephone/video signal to a remote station for analysis, or transmitted or recorded as computer data or graphics data.

Various systems and apparatus may be used to analyse the video recordings. The degree of complexity and automation of the analysis will depend on the required accuracy of the measurements and on whether or not the analysis is to be performed by an operator skilled in biomechanics. The video recordings made by the recording apparatus lend themselves to analysis by a computer aided graphics system.

Figure 4:
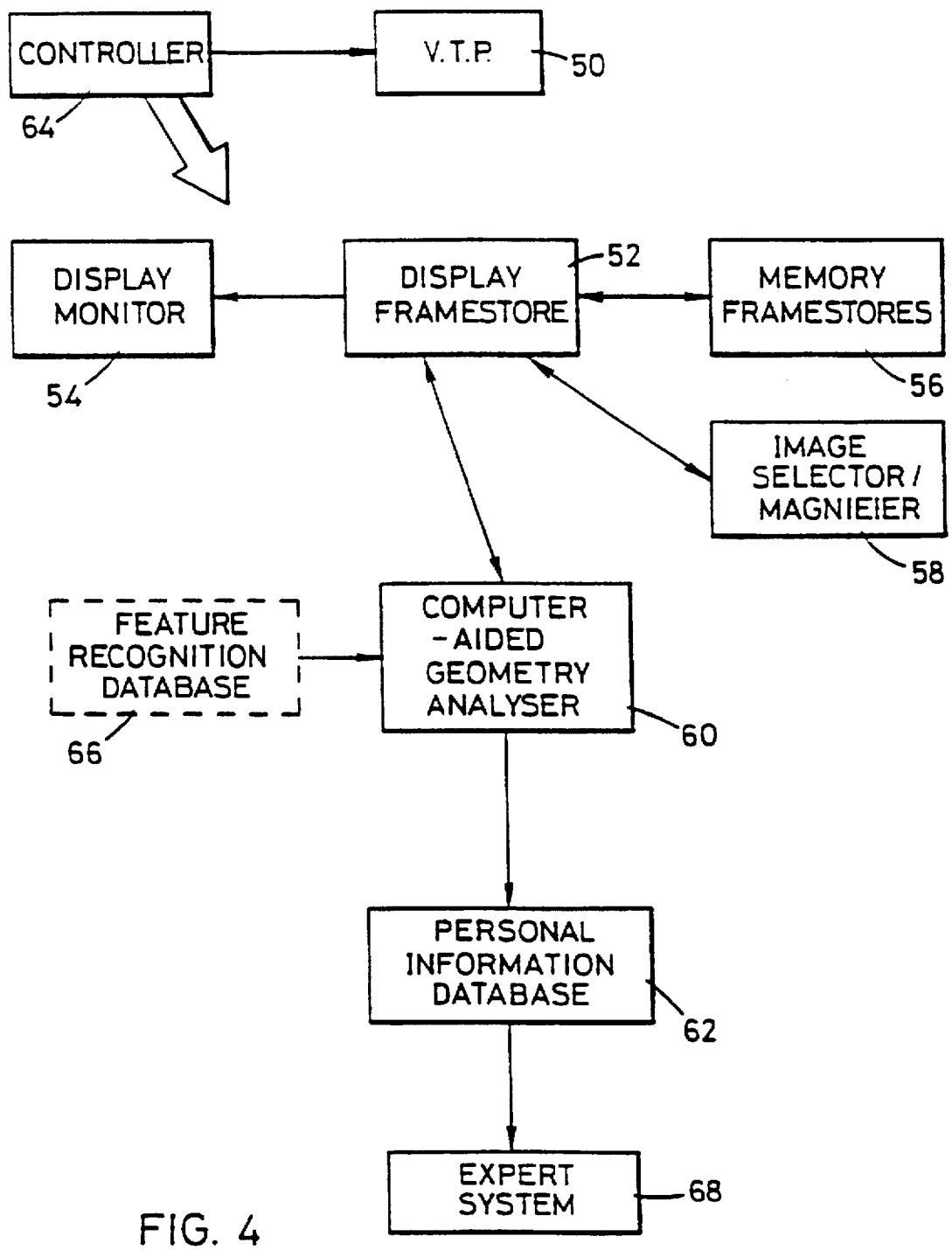
FIG. 4 is a block diagram of an apparatus for analysing the results from the apparatus of FIG. 2.

FIG. 4 illustrates one form of apparatus 48 for analysing the video recordings. It includes a video tape player 50 for playing back the tape recorded with the apparatus of FIG. 2. One or more additional, or alternative, video or graphics information inputs (not shown) may be provided (for example, a modem link) depending on how the video signal recorded above is to be forwarded or sent for analysis.

The apparatus 48 comprises a digital display framestore 52 into which the video signal is fed. The display framestore 52 provides an output to a video monitor 54 for display. The apparatus also comprises a bank of memory framestores 56 in which a number of video frames can be stored, and an image selector/magnifier 58 which can process video data to select, enlarge or reduce portions of the video frame. The apparatus also comprises a computer-aided geometry analyser 60 which can calculate distances and angles between selected points and lines marked on the video images.

The apparatus also includes a database memory 62 for storing sets of results for a particular person, calculated by the geometry analyser 60.

The apparatus 48 operates under the control of a controller 64. This includes a manual input means (not shown) for example, in the form of a keyboard or a computer mouse by which a person can input commands to control the apparatus.

The apparatus of FIG. 4 may be embodied as dedicated digital processing and video processing circuitry. It may also be embodied by a programmed computer with a graphics capability configured to perform the above, or by a combination of a computer and dedicated graphics circuitry.

Figure 5:
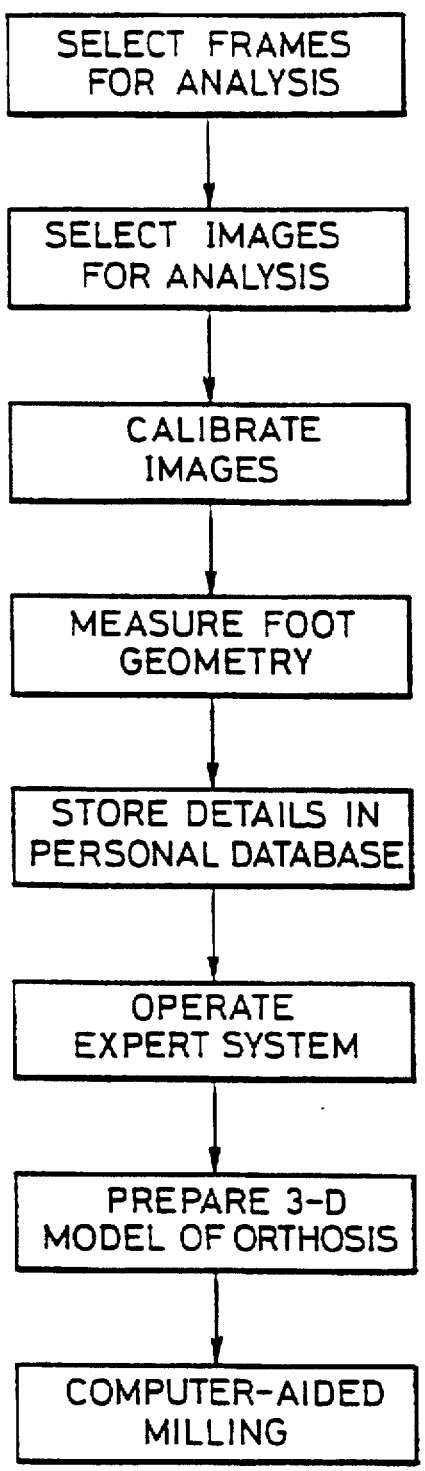
FIG. 5 is a block diagram of the process for operating the apparatus of FIG. 4.

In use, referring to FIGS. 4 and 5, the process of analysis begins by selecting a number of frames from the input video signal, which are to be used for analysis. Each frame includes approximately four concurrent images. The selection is achieved by an operator viewing the video signal in slow motion, frame by frame, for example by using the controller 64 and the display framestore 52.

The operator selects frames in which the foot is in one of a plurality of predetermined reference positions which illustrate the behaviour of the foot. Such positions include the sub talor joint neutral position which is used conventionally for making casts, but they also include other positions from which the range of foot movement and the characteristics of foot under different stationary/kinetic conditions can be observed.

The four concurrent images in each frame enable the operator to observe the foot from different directions, effectively in three dimensions. Thus the operator can select the individual frame or frames in which the foot is in precisely the correct position for analysis.

It will be appreciated that if only one image was being viewed, it might be difficult for the operator to decide which frame represented the precise moment when the foot was in one of the reference positions. For example, by referring to the front view only, it is difficult to detect when the heel of the foot is pressed down. However, by displaying simultaneously the recorded views from the different directions, i.e. from the front, rear, side and underneath, it is possible to determine accurately the foot's position in three dimensions. Frames which are selected for later use can be stored in the memory framestores 56. Typically about 30 frames would be selected at this stage.

The next stage is for the operator to select specific images for analysis from the frames selected in the above procedure. Under the control of the controller 64, the operator can select one or more images from each frame for further analysis. Typically, the images will be selected using the selector/magnifier 58.

For each frame, it is likely that only one, two or perhaps three of the four images will contain geometric information of interest. The four images when viewed together determine the precise position of the foot at that instant, but not all of the four images may be suitable for geometric analysis.

Each selected image should be magnified so that it occupies the whole of the available display area of the monitor 54 (and of the display framestore 52). If only a portion of a selected image is required for further analysis, that portion should be further magnified to occupy the whole of the display area, and the remainder of the image can be cropped. The selected images can then be restored, for example, in the memory framestores 56. Typically about 40 images would be selected.

The next stage in the analysis is for each selected image to be studied, and the geometric details to be measured. This can either be done manually, automatically or semi-automatically with the assistance of the operator. Before each image can be studied, the geometry analyser has to be calibrated according to the scale of the video image. Calibration is based on the graticule grid pattern of the platform 22 which will be included in the recorded video images.

During semi-automatic operation of the geometry analyser 60, the operator identifies the position of certain key points on the image of the foot as viewed on the display framestore 52. The operator may select these points by moving a computer-mouse which controls a position cursor, or a line cursor, on the displayed image.

Figure 6:
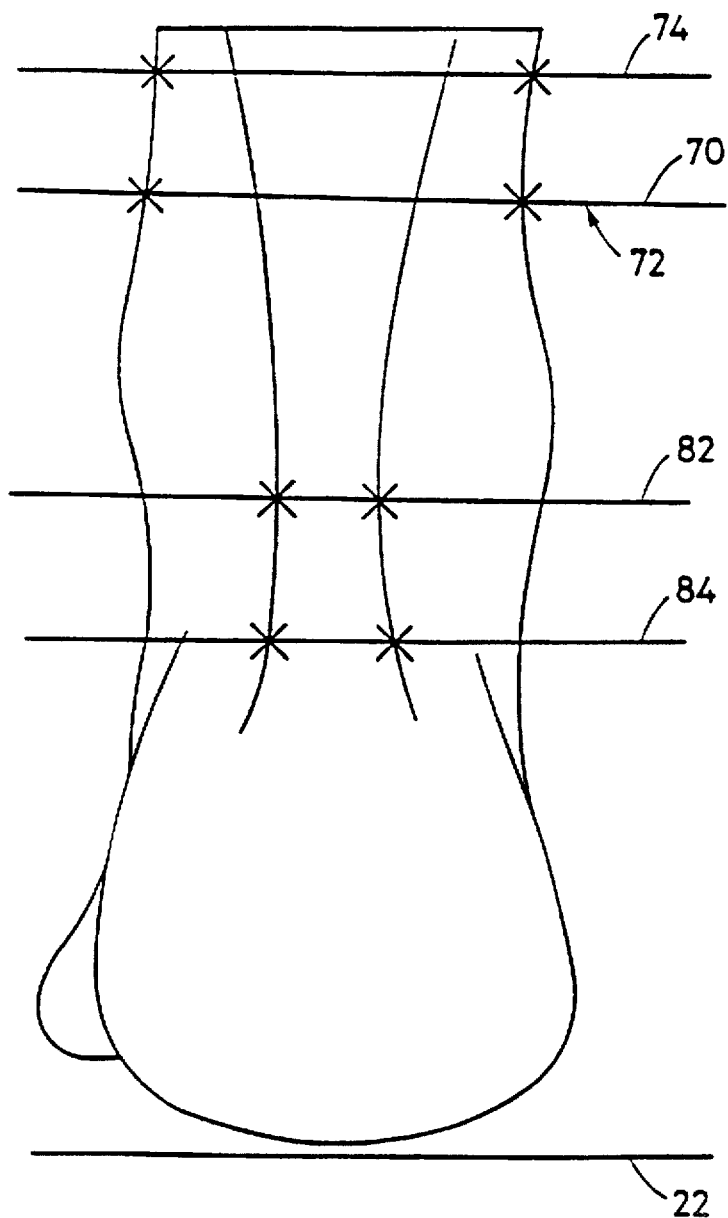
FIGS. 6 and 7 are diagrammatic views illustrating geometric analysis of a sample image.
Figure 7:
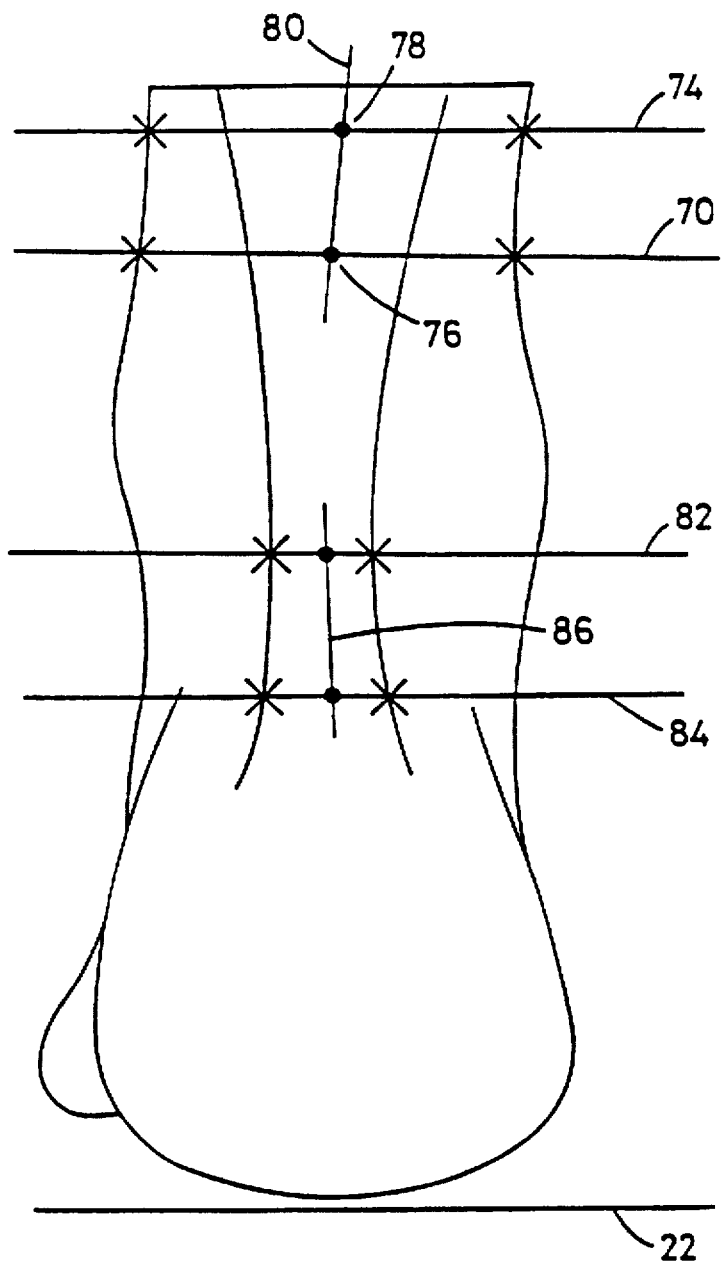

FIGS. 6 and 7 illustrate one form of geometric analysis on a rear-view image of a person's foot using semi-automatic operation. In FIG. 6 a line cursor 70 is moved to a first point 72 at which the Achilles' tendon meets the heel bone as viewed in the displayed position. A second line cursor 74 parallel with the front is drawn on the image automatically by the geometric analyser. The operator marks the "edge definition" point "X" on the image at which the cursor lines 70 and 74 meet the edge of the image. Once these points have been entered, the geometric analyser calculates mathematically the Tibial Varum Angle, see FIG. 7. The calculation is performed automatically by (i) calculating the midpoint 76 between the edge definition points "X" marked for the first line cursor 70; (ii) calculating the midpoint 78 between the edge definition points "X" marked for the second line cursor 74; (iii) constructing a bisector line 80 passing through the midpoints 76 and 78 calculated above; and (iv) measuring the angle which the bisector line 80 makes with an imaginary vertical line.

Referring again to FIG. 6, the positioning of two more line cursors 82 and 84 (the latter being drawn and positioned automatically relative to the first) is used to determine the Varus and Valgus angles for the foot. In a similar manner to that described above, the operator marks the "edge definition" points "X" at which the line cursors 82 and 84 meet the edge of the image. The geometric analyser calculates the midpoints between the "edge definition" points, constructs a bisector line 86, and measure the angle between the bisector line 86 and the vertical.

For fully automatic operation, a recognition database 66 will be provided to provide recognition information to the apparatus to enable the reference points on the image to be located automatically. In particular, the system may be programmed to detect or determine the edges of a person's foot in the recorded image, and to generate a surface contour representation of the three-dimensional shape of the foot contained in the images. Thus, the amount of any external input required from the operator can be reduced to a minimum for geometric analysis.

In short, it will be apparent to the skilled man that at least the same degree of geometric information can be obtained from the images as would be obtainable from conventional foot-casting techniques. It will be apparent to the skilled man precisely what information is required in order to define an appropriate functional orthotic. However, with the invention, the amount of information made available by the use of the cameras far exceeds the amount of information derivable by conventional casting techniques.

Since the memory framestores 56 can hold quite a large number of images, the geometric analysis for certain characteristics may be repeated several times using different images. The results can then be statistically averaged to improve the accuracy of the determinations. This will be particularly advantageous in cases where it is apparent from the video images that critical joints of the foot are incapable of adequate motion. Characteristics may be calculated in different positions of the foot, and the results compared with each other.

The results can be fed into the information database 62 in which information is collected for each of the person's feet.

The characteristics may then be fed to an expert system 68 which is programmed to deduce from the measured characteristics appropriate parameters for a functional orthosis to match the foot being studied. The expert system assesses the degree to which the foot deviates from a normal or ideal foot, and also assesses the amount of orthotic control the foot requires. It also assesses the amount of control the foot is capable of accepting. The expert system may be implemented entirely with a programmed computer, or it may be an interactive computer-aided system which is operated by a skilled practitioner.

The expert system 68 provides as its output the prescription data for the design and shape of a pair of functional orthoses, each one being customised to match an individual foot. In this exemplary embodiment, the output data is provided in the form of a three dimensional data model for each orthosis. Thus the system of the preferred embodiment is able to take advantage of the recent developments in computer-aided manufacture (CAM). The precise form of the data for the three-dimensional model will depend on the requirements of the manufacturing machines, but one form which is envisaged in particular is a "wire-cage" representation defining the outline in three-dimensions.

In one type of manufacturing process, the orthotic device is milled from a carbon-epoxy block rather than by using more conventional thermoplastics. Using the 3-dimensional prescription data, an accurate replica article can be manufactured automatically and as a relatively quick process. The article can be milled down to give the appropriate thicknesses for resilience/rigidity as prescribed for the person's foot.

It will be appreciated that other manufacturing processes (including manual processes) could be used for the fabrication of each orthotic device. However, the present invention lends itself to being able to provide the appropriate prescription and design information in a form matched to a particular fabrication system.

It will be appreciated that the technique of the present invention to record a person's foot by using video camera positioned to obtain three-dimensional information enables simple and accurate measurements to be taken from a person's foot. It avoids the need for major assumptions and approximations as used in the prior art. The operator does not need to be skilled in the art of biomechanics. Also, the technique does not rely on difficult co-operation from the person who's foot is being analysed, and in particular it avoids the need for the person to have to remain in a predetermined position without movement.

During analysis, the images of the foot can be "frozen" at precisely the right moment which provides ideal geometric characteristics for measurement and analysis. Using computer-aided technology, measurements can be made much more accurately than with the manual protractor type methods used in the prior art. Finally, it is possible to study the foot in any of the positions in which it has been recorded, to observe range of movement and abnormal joint behaviour.

As a modification to the embodiment described above, a thermal camera may be provided to detect "hot spots" on the person's foot or other part of the body. The thermal camera may be included as an integral thermal/video camera in the place of one of the video cameras, or it may comprise a separate dedicated camera providing an additional recording signal.

As shown phantom in FIG. 2, one or more further video cameras 90 may be provided to view middle and upper portions of the person's body as the person performs the foot exercises. Such additional cameras may be useful for observing shoulder, spinal and general back motion, for example, for a chiropractor. The cameras 90 may be adjustable to view at any angle of elevation, and in any direction as desired. The signals from the further cameras may be multiplexed and indexed with the signals from the foot cameras, or it may be recorded and processed separately.

The technique of this invention also permits the design of the functional orthotic to be matched to different footwear required by the subject person. For example, individual devices may be required for sports footwear, dress footwear, and casual footwear. The invention permits functional orthotics to be adapted to the "footwear" characteristics as well as to the orthotic characteristics of the person's foot.

Although in the embodiment described above, the control of the lighting projectors 25 and 27, and of the indexer 46 is performed automatically, it will be appreciated that the control may have a manual override, or it may be entirely manual.

It will also be appreciated that in accordance with the principles of the present invention (particularly as described in the preferred embodiment) a person's foot can be measured, and an orthotic device prescribed, with a much greater accuracy and reliability than with some conventional methods. The "weak points" of the conventional methods can thereby be avoided to improve the standard of quality.

It will be appreciated that the above description of the invention is merely illustrative of a preferred embodiment, and modifications of detail may be made without departing from the scope, or principles or spirit of the invention.

We claim:

1. A method of measuring orthotic characteristics of a person's foot, comprising:

projecting a pattern of light markers onto the foot;

providing a plurality of video cameras for viewing the foot from a plurality of different look directions;

recording the shape and appearance of the foot substantially in real time by using the video cameras concurrently to provide video images containing information in three dimensions; and analysing the video images to obtain the desired measurements.

2. A method according to claim 1, wherein the cameras view the foot from positions which are substantially at 90° to the cardinal body planes.

3. A method according to claim 1 or 2, wherein the cameras are positioned to view the foot from one or more of: below the foot; in front of the foot; behind the foot; at the side of the foot.

4. A method according to claim 1 or 2, wherein the step of analysing comprises digitising at least some of the video images, and utilising a computer aided graphics system to analyse at least some of the digitised images.

5. A method for making a record of a person's foot for a functional orthosis, comprising:

projecting a pattern of light markers onto the foot;

providing a first video camera to view the foot from the underside;

providing a second video camera to view the foot from the rear;

providing a third video camera to view the foot from a side;

providing a fourth video camera to view the foot from the front; and recording the shape and appearance of the foot substantially in real time by using the video cameras concurrently to provide video images containing information in three dimensions.

6. A method according to claim 5, further comprising multiplexing the signals from the cameras to provide a single combined signal.

7. A method according to claim 6, further comprising recording the combined signal on a video signal recording medium.

8. An apparatus for making a record of a person's foot for a functional orthosis, comprising:

a platform on which a person may stand or may place the foot to be recorded, at least a portion of the platform being transparent;

means for projecting a pattern of light markers onto the foot;

a first video camera at a first position to view the underside of the foot through the transparent portion of the platform;

a second video camera at a second position for viewing the foot from the rear;

a third video camera at a third position for viewing the foot from a side;

a fourth video camera at a fourth position for viewing the foot from the front; and means for operating the cameras concurrently for recording the shape and appearances of the foot substantially in real time to provide video images containing information in three dimensions.

9. Apparatus according to claim 8, further comprising a multiplexer for combining the signals from the cameras to provide a single combined signal.

10. Apparatus according to claim 9, further comprising means for recording the combined signal on a video signal recording medium.

11. Apparatus according to claim 8, 9 or 10, further comprising means for indicating the contact regions of a person's foot when the person is standing on the platform.

12. A method for determining characteristics of a person's foot, comprising:

projecting a pattern of light markers onto the foot;

providing a sequence of video images frame by frame of said foot;

selecting a frame for analysis;

defining predetermined points on the image depicted in the frame selected for analysis; and calculating mathematically one or more geometric characteristics of the person's foot based on the points defined in the image.

13. A method according to claim 12, wherein the video images are digitised.

14. A method according to claim 12 or 13, further comprising a step of calibrating the video images based on a marker or scale contained in at least one image.

15. A method according to claim 12, 13 or 14, wherein each frame comprises a plurality of concurrent images corresponding to different simultaneous views of a person's foot, and the method further comprises selecting at least one of the images for analysis from the plurality of images.

16. Apparatus for determining characteristics of a person's foot, comprising:

means for projecting a pattern of light markers onto the foot;

means for providing a sequence of video images of the foot frame by frame;

means for selecting a frame for analysis;

means for defining predetermined points on the image depicted in the frame selected for analysis; and means for calculating mathematically one or more characteristics of the person's foot based on the points defined in the image.

17. Apparatus according to claim 16, further comprising means for calibrating the mathematical calculating means based on a marker or scale contained in at least one image.

18. Apparatus according to claim 16 or 17, wherein each frame comprises a plurality- of concurrent images corresponding to different simultaneous views of a person's foot, and the apparatus further comprises means for selecting at least one image for analysis from the plurality of images.

19. A method of measuring orthotic characteristics of a person's foot, comprising:

projecting a pattern of light markers onto the foot;

providing a sequence of video images frame by frame of the foot;

measuring geometric characteristics of the foot from one or more of the video frames; and comparing the measured geometric characteristics with a set of reference characteristics to determine deviation from normality.

* * * * *